United States Patent [19]

Marcovina et al.

[11] Patent Number: 5,712,157
[45] Date of Patent: Jan. 27, 1998

[54] METHODS AND MATERIALS FOR THE IMMUNOASSAY OF APOLIPOPROTEIN(A) AND LIPOPROTEIN(A)

[75] Inventors: Santica M. Marcovina; John J. Albers, both of Seattle, Wash.

[73] Assignee: University of Washington, Seattle, Wash.

[21] Appl. No.: 360,234

[22] Filed: Dec. 20, 1994

[51] Int. Cl.$^6$ .............................. C07K 16/18; C12N 5/20
[52] U.S. Cl. ................. 435/337; 530/388.25; 530/389.3; 935/89; 935/95; 935/104
[58] Field of Search ...................... 435/240.27, 337; 530/388.25, 389.3; 935/89, 95, 104

[56] References Cited

PUBLICATIONS

Albers, J.J. et al., "The Unique Lipoprotein(a): Properties and Immunochemical Measurement," *Clin. Chem.* 36(12):2019–2026 (1990).
McLean, J.W. et al., "cDNA sequence of human apolipoprotein(a) is homologous to plasminogen," *Nature* 330:132–137 (1987).
Guevara, J. et al., "A Structural Assessment of the Apo[a] Protein of Human Lipoprotein[a]," *Proteins: Structure, Function, and Genetics* 12:188–199 (1992).
van der Hoek, Y.Y. et al., "The apolipoprotein(a) kringle IV repeats which differ from the major repeat kringle are present in variably-size isoforms," *Human Molecular Genetics* 2(4):361–366 (1993).
Lackner, C. et al., "Molecular definition of the extreme size polymorphism in apolipoprotein(a)," *Human Molecular Genetics* 2(7):933–940 (1993).
Albers, J.J. and Hazzard, W.R., "Immunochemical Quantification of Human Plasma Lp(a) Lipoprotein," *Lipids* 9(1):15–26 (1974).
Albers, J.J. et al., "Radioimmunoassay of human plasma Lp(a) lipoprotein," *J. Lipid Res.* 18(3):331–338 (1977).
Gaubatz, J.W. et al., "Human Plasma Lipoprotein[a]. Structural Properties," *J. Biol. Chem.* 258(7):4582–4589 (1983).
Rainwater, D.L. and Manis, G.S., "Immunochemical characterization and quantitation of lipoprotein(a) in baboons. Development of an as depending on two antigenically distinct proteins," *Atherosclerosis* 73:23–31 (1988).
Wong, W.L.T. et al., "A Monoclonal-Antibody-Based Enzyme-Link Immunosorbent Assay of Lipoprotein(a)," *Clin. Chem.* 36(2):192–19 (1990).
Vu-Dac, N. et al., "Latex immunoassay of human serum Lp(a$^+$) lipoprotein," *J. Lipid Res.* 26:267–268 (1985).
Cazzolato, G. et al., "The determination of lipoprotein Lp(a) by rate and endpoint nephelometry," *Clinica Chimica Acta* 135:203–208 (1983).
Vu Dac, N. et al., "A Selective bi-site immunoenzymatic procedure f human Lp[a] lipoprotein quantification using monoclonal antibodies against apo[a] and apoB," *J. Lipid Res.* 30:1437–1443 (1989).
Albers, J.J. et al., "Evaluation of a monoclonal antibody-based enzym linked immunosorbent assay as a candidate reference method for the measurement of apolipoprotein B-100," *J. Lipid. Res.* 30:1445–1458 (1989).
Marcovina, S.M. et al., "Identification of 34 apolipoprotein(a) isoforms: differential expression of apolipoprotein(a) alleles between American blacks and whites," *Biochem. Biophys. Res. Comm.* 191(3):1192–1196 (1993).
Albers, J.J. and Marcovina, S.M., "Lipoprotein(a) quantification: comparison of methods and strategies for standardization," *Current Opinion in Lipidology* 5:417–421 (1994).
Marcovina, S.M. et al., "Effect of the Number of Apolipoprotein(a) Kringle 4 Domains on Immunochemical Measurements of Lipoprotein(a)," *Clin. Chem.* 41(2):246–255 (1995).
Theolis et al., *J. Immun. Meth.*, 1994, 172:43.
Lafferty et al., *J. Lipid. Res.*, 1991, 32:277.
Wong et al. *Clin Chem.*, 36(2):192, 1990.

*Primary Examiner*—Frank C. Eisenschenk
*Attorney, Agent, or Firm*—Christensen O'Connor Johnson & Kindness PLLC

[57] ABSTRACT

The present invention relates to monoclonal antibodies and a method for the quantification of apolipoprotein(a) and lipoprotein(a) present in human body fluids. The method is not sensitive to the presence of plasminogen or the apo(a) kringle 4 repeats. The assay involves the addition of the test sample to an immobilized anti-apo(a) antibody and forming a first immobilized complex of apolipoprotein(a)/anti-apo(a) first antibody, contacting first immune complex with an anti-apo(a) monoclonal antibody specific for apo(a) with no crossreactivity to plasminogen and which does not identify the kringle 4 type 2 apo(a) repeats and thereafter quantitating apo(a) based on the amount of bound anti-apo(a) monoclonal antibody. Immobilized goat or rabbit anti-human apo(a) antibody can be employed as the first capture antibody and the mouse anti-apo(a) monoclonal antibody as second antibody. The amount of anti-apo(a) monoclonal antibody bound is quantitated through binding of a third antibody enzyme conjugant, e.g., goat anti-mouse antibody/horseradish peroxidase (HRP) conjugate, followed by reaction with a suitable substrate such as o-phenylenediamine dihydrochloride.

2 Claims, 2 Drawing Sheets

METHODS AND MATERIALS FOR THE IMMUNOASSAY OF APOLIPOPROTEIN(A) AND LIPOPROTEIN(A)

This invention was made with government support under National Institutes of Health Grant No. HL30086. The government has certain rights in the invention.

FIELD OF THE INVENTION

The present invention relates generally to immunoassays for apolipoprotein(a) [apo(a)] and lipoprotein(a) [Lp(a)]. More particularly, the present invention relates to improved assays for the detection and quantification of apo(a) and Lp(a) in fluid samples and to new monoclonal antibodies for use in the assays.

BACKGROUND OF THE INVENTION

Lipoprotein(a) or Lp(a) is a lipoprotein particle containing a lipid core and single molecule of apo B-100 disulfide linked to a unique protein called apolipoprotein(a) or apo(a). (Albers et al., 1990). The presence of apo(a) distinguishes Lp(a) from all other lipoproteins. The structure of apo(a) has a profound impact on the measurement of Lp(a). Not only is apo(a) highly glycosylated but it also exhibits considerable size and structural heterogeneity. Apo(a) contains three structural domains each highly homologous with domains of plasminogen (McLean et al., 1987). Apo(a) contains multiple copies of a domain homologous to Kringle 4 (K4) of plasminogen and single copy of a domain highly homologous but not identical to Kringle 5 of plasminogen. The cDNA sequence analyses of apo(a) indicates that among the K4 components, amino acid sequence differences are evident, although they have a high degree of amino acid homology with each other. Based on the amino acid sequence differences, ten different K4 types have been identified (Guevara et al., 1992). K4, type 1 and K4 types 3 through 10 each appear to have one copy present in each individual while the K4 type 2 is present in a variable number of repeats and is responsible for the size differences in apo(a) (van der Hoek et al., 1993, and Lackner et al., 1993). Although the function of Lp(a) is not known, numerous clinical studies have demonstrated that high serum concentrations of Lp(a) are associated with both coronary and cerebral vascular disease (Albers et al., 1990).

Numerous methodological approaches have been used for measurement of apo(a) and Lp(a) in human body fluids as summarized by Albers et al. (*Clin. Chem.* 36:2019–2026 (1990)). The first quantitative assay for Lp(a) was a radial immunodiffusion (Albers and Hazzard, *Lipids* 9:15–26 (1974)). However, this assay did not have the required sensitivity to measure Lp(a) in all plasma samples and therefore, Albers et al. (*J. Lipid Res.* 18:331–338 (1977)) developed a sensitive radioimmunoassay which was able to quantitate Lp(a) in all plasma samples. Since that time numerous other methodological approaches have been developed for the measurement of Lp(a) including electroimmunoassay (Gaubatz et al., *J. Biol. Chem.* 258:4582 (1983)), enzyme-linked immunoassay (Rainwater and Manis, *Atherosclerosis* 73:23–31 (1988); Wong et al., *Clin. Chem.* 36:192–197 (1990)), immunoturbidity (VuDac et al. *J. Lipid Res.* 26:267–269 (1985)), and immunonephelometry (Cazzolato et al., *Clin. Chem. Acta.* 135:203–208 (1983)).

The previously described assays for Lp(a) that are based on the detection of apo(a) in the test sample can potentially measure plasminogen because plasminogen has high sequence homology to apo(a) and most polyclonal antibodies and some monoclonal antibodies have crossreactivity with plasminogen. One approach that has been used to avoid potential crossreactivity with plasminogen has been to measure Lp(a) using ELISA with the capture antibody directed to apo(a) and with the detecting antibody directed to the apo B component of Lp(a) (Rainwater and Manis, *Atherosclerosis* 73:23–31 (1988); VuDac et al., *J. Lipid Res.* 30:1437–1443 (1989)). These latter assays do not measure apo(a) that is not complexed with apo B but measure the apo(a)/apo B-100 complex found in Lp(a). Another approach to avoid potential crossreactivity with plasminogen is to use as the detecting antibody a monoclonal antibody that has been selected not to crossreact with plasminogen.

Other potential problems with immunoassays that detect apo(a) are that these methods may be sensitive to the differences in size of apo(a). Methods that use an apo(a) indicator antibody that recognize the Kringle 4 type 2 repeats would be highly sensitive to changes in Lp(a) size, and can not be used to accurately quantify apo(a). Thus, there remains in the art a need for immunoassays for apo(a) which do not crossreact with plasminogen and are not sensitive to differences in apo(a) size.

SUMMARY OF THE INVENTION

The present invention relates to a methods for the quantification of apo(a) and Lp(a) present in body fluids by contacting a fluid sample with an anti-apo(a) antibody that does not react with the K4 type 2 repeats of apo(a) and does not crossreact with plasminogen, to form an antibody/apo(a) complex, and then measuring the amount of complex formed as an indication of the amount of apo(a) in the fluid sample. In one representative embodiment, a fluid sample is contacted with an immobilized anti-apo(a) first antibody to form an immobilized first complex of apo(a)/anti-apo(a) first antibody. The first complex is then contacted with an anti-apo(a) second antibody to form a second immobilized complex, and thereafter the presence or amount of apo(a) is determined based on the presence or amount of bound anti-apo(a) second antibody in second complex. It is presently preferred that the first anti-apo(a) and the second anti-apo(a) antibodies be directed against human apo(a), that the first anti-apo(a) to be provided in the form of IgG preparations derived from the polyclonal antisera and that the second anti-apo(a) antibody be a monoclonal antibody specific for apo(a) that does not crossreact with plasminogen and that does not react with the K4 type 2 repeats of apo(a). In a particularly preferred embodiment of this aspect of the invention, the second antibody is monoclonal antibody a-40 produced by hybridoma a-40, ATCC No. CRL 11759. Quantification of the second antibody may be achieved through the use of an enzyme labeled third antibody, which is immunoreactive with the second antibody.

In other aspects, the present invention provides monoclonal antibodies, such as the antibody designated a-40, provided by hybridoma a-40, ATCC No. CRL 11759, that do not react with the K4 type 2 repeats of apo(a) and do not crossreact with plasminogen. The antibodies of the invention are highly useful in determining the presence or amount of apo(a) in test samples, as is detailed herein.

Other aspects and advantages of the present invention will be apparent upon consideration of the following detailed descriptions.

BRIEF DESCRIPTION OF THE DRAWINGS

The foregoing aspects and many of the attendant advantages of this invention will become more readily appreciated

DETAILED DESCRIPTION OF THE PREFERRED EMBODIMENT

Figure 1:
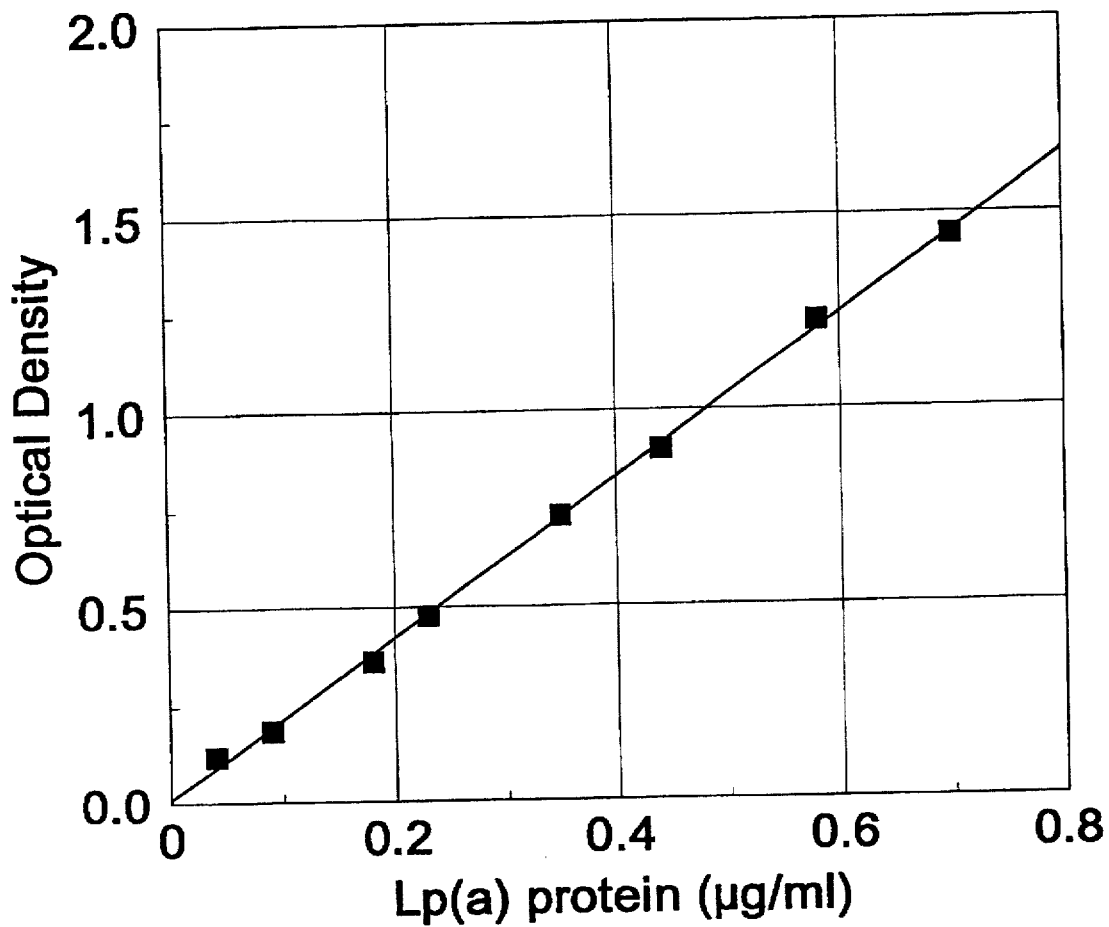
FIG. 1 is a standard curve of absorbance at 495 nM plotted against lipoprotein(a) concentration for an assay performed in accordance with Example 3.

In one aspect of the present invention, monoclonal antibodies are provided that are characterized by their specific reactivity with human apolipoprotein(a) and lipoprotein(a) but that do not react with Kringle 4 type 2 domain of apo(a) and do not exhibit immunological cross-reactivity with human plasminogen or apolipoprotein B. A representative embodiment of this aspect of the invention is monoclonal antibody a-40, produced by hybridoma a-40, ATCC No. CRL 11759.

Monoclonal antibodies of the invention can be prepared according to conventional methods by using human lipoprotein(a) purified from human serum or plasma as an antigen. In the preparation of antibodies of the present invention, lipoprotein(a) is not necessarily highly purified. It is possible to use a relatively crude product containing the lipoprotein(a). In a specific preferable example of the preparation of antibody of the present invention, transformed mammal cells immuned by lipoprotein(a) as an immune antigen are fused with mammal plasmacytoma to produce hybridomas. A clone recognizing the lipoprotein(a) is selected from the hybridomas. The target monoclonal antibody is then obtained from the clone. In the above process, there are few limitations to the mammal cells to be transformed with the immune antigen, i.e., the lipoprotein(a). It is desired that the immune antigen be selected taking its compatibility with the mammal plasmacytoma to be fused into consideration. Mice, rats, and the like are generally preferably used.

Immunization may be carried out according to conventional methods well known to those skilled in the art, e.g., by intravenously or intraperitoneally injecting the lipoprotein (a) into an animal. More specifically, lipoprotein(a) may be diluted with PBS or physiological saline to a suitable concentration, and then injected into the animal, together with a suitable adjuvant, if necessary, several times at an interval of 2-21 days until the total amount injected reaches 1-100 µl/animal. A conventional carrier may be used for the injection. Spleen cells enucleated from the animal 3 days after the completion of the injection of lipoprotein(a) is desirable for use as immune cells.

Various known myeloma cells can be used as mammal plasmacytoma to be fused with the above immune cells. Such myeloma cells include, for example, p3 (pe/x63-Ag8) (*Nature*, 256:495–497 (1975)), P3-U1 (*Current Topics of Microbiology and Immunology*, 81:1-7 (1987)), NS-1 (*Eur. Immunol*, 6:511-519 (1976)), MPC-11 (*Cell*, 8:405–415 (1976)), PS2/0 (*Nature*, 276:269:270 (1978)), FO (*J. Immunol. Meth.*, 35:1-21 (1980)), x63, 6, 5, 3 (*J. Immunol.*, 123:1548–1550 (1979)), S194 (*J. Exp. Med.*, 148:313-323 (1978)), and R210 (*Nature*, 277:131-133 (1979)) of rat, and the like.

The fusion of the immune cell and the plasmacytoma can be carried out basically in accordance with known methods, for example, by the method of Milestein et al. (*Methods Enzymol.*, 73:3–46 (1981)), in the presence of a fusion accelerator and in a conventional nutritious medium. Conventional fusion accelerators, e.g., polyethylene glycol (PEG), sendai virus (HVJ), etc., can be used, optionally with the addition of adjuvants such as dimethylsulfoxide and the like in order to promote the efficiency of the fusion. A fusion ratio of the immune cells and the plasmacytoma may be the conventional ones, e.g., about 1-10 immune cells per one plasmacytoma. As a medium for the fusion, any medium used for the cultivation of the plasmacytoma, e.g., PRMI 1640 medium, MEM medium, as well as other various media used for the cultivation of this type of cells can be used. Serum obtained by removing serum complement from fatal calf serum (FCS) is a typical example of the medium. The fusion is carried out by thoroughly mixing a prescribed amount of the immune cells and the plasmacytoma and blending this mixture with a medium to which about 30–60% (w/v) of a PEG (e.g., PEG with an average molecular weight of 1,000–6,000) solution which has been heated to about 37° C. in advancemis added. The cultivation in the HAT medium is continued for a period sufficient for cells other than hybridoma (e.g., unfused cells) to die, usually for several days to several weeks. Hybridoma thus obtained is subjected to a conventional limiting dilution method to detect the target cell line producing the antibody and to monocloning.

The detection of the antibody-producing cell lines of the invention is carried out according to a standard method commonly used for the detection of antibodies (Hybridoma and Monoclonal Antibody, R&D Planning Co., 30–53 (1982)), such as, for example, the ELISA method (Engvall, E., *Methods Enzymol.*, 70:419–439 (1980)), the plaque method, the spot method, the agglomeration reaction method, the Ouchterlony method, the radio immunoassay (RIA), and the like. Use of the above lipoprotein(a) as an antigen for the detection is desirable. Thus, antibody-producing cell lines are screened to obtain those cell lines that generate antibody having binding specificity for apo(a), but that do not react with the K4 type 2 repeats of apo(a) and that do not crossreact with plasminogen.

Hybridomas producing target monoclonal antibodies of the invention can be cultivated over generations in conventional media and can be stored in liquid nitrogen for a long period of time.

Collection of monoclonal antibodies of the present invention from hybridomas of the invention can be performed by cultivating the hybridoma according to a conventional methods and obtaining the monoclonal antibody as a supernatant or by administering the hybridoma to a mammal with which the hybridoma is compatible to proliferate and by collecting the desired antibodies from the ascites fluid. The former method is adaptable to the production of high purity monoclonal antibody and the latter to mass production of monoclonal antibody. Monoclonal antibodies thus obtained may be purified by means of salting, gel filtration, affinity chromatography, or the like, as is well known in the art.

Human lipoprotein(a) can be analyzed at a high sensitivity and precision and with a high specificity in a simple manner by the use of monoclonal antibodies of the invention in conventional immunoassay formats, such as enzymatic immunoassays (EIA), enzyme-linked immunosorbent assays (ELISA), radioimmunometric assays (RIA), immunoturbidimetric assays, or the like. Because the monoclonal antibodies of the present invention react with human lipoprotein(a) with specificity and do not exhibit an immunological cross-reactivity with plasminogen and apoprotein B, they are useful for the determination of human lipoprotein (a) in clinical samples by immunoassay, particularly by immunoturbidimetry, thus enabling to screen various heart diseases and to diagnose the status of the diseases. Thus, the present invention further provides various immunoassay methods for determining the presence or amount of lipoprotein(a) or apolipoprotein(a) in a biological fluid sample using a monoclonal antibody of the invention. The antibody comprises immunochemical reagents for forming an immunoreaction product whose presence or amount relates, either directly or indirectly, to the presence or amount of lipoprotein(a) or apolipoprotein(a) in the sample. Those skilled in the art will appreciate that there are numerous well known clinical diagnostic chemistry procedures in which the immunochemical reagents of this invention can be used to form an immunoreaction product whose presence and/or amount relates to the presence and/or amount of lipoprotein(a) or apolipoprotein(a) present in a body sample.

While exemplary assay methods are described herein, the invention is not so limited. Various heterogenous and homogenous protocols, either competitive or noncompetitive, can be employed in performing an assay method of this invention. For example, in one illustrative embodiment, a double antibody or "sandwich" immunoassay format may be employed comprising the steps of: (a) forming a first immunoreaction admixture by admixing a vascular fluid sample with a first antibody, e.g., a monoclonal antibody, wherein the antibody and apoliproprotein(a) present in the sample are capable of forming a first immunoreaction product (the first antibody can be operatively linked to a solid matrix); (b) maintaining the first immunoreaction admixture so formed under biological assay conditions for a time period sufficient to form the first immunoreaction product (the first immunoreaction product can then be separated from the sample); (c) forming a second immunoreaction admixture by admixing the first immunoreaction product with a second antibody, monoclonal or polyclonal, which recognizes lipoprotein(a) or apolipoprotein(a); (d) maintaining the second immunoreaction admixture so formed under biological assay conditions for a period sufficient to form the second or "sandwich" immunoreaction product; and (e) determining the presence and, optionally, the amount of second immunoreaction product formed, and thereby the presence and, optionally, the amount of lipoprotein(a) or apolipoprotein(a) in the sample. Preferably, the second antibody is labeled, preferably with an enzyme, and thus the second immunoreaction product formed will be a labeled product to facilitate determination of the second immunoreaction product. Thus, the presently preferred method according to the invention employs immobilized goat anti-human apo(a) antibody as first capture antibody and mouse monoclonal anti-apo(a) antibody as the second antibody. The amount of anti-apo(a) monoclonal antibody bound is quantitated by the formation of a third immobilized complex involving the use of a third antibody enzyme conjugate, e.g., goat anti-mouse horseradish peroxidase (HRP) conjugate followed by reaction with a suitable substrate such as o-phenylenediamine dihydrochloride. An alternative approach can employ the specific anti-apo(a) which does not react with plasminogen or the K4 type 2 repeats of apo(a) coupled to organic polymer latex particles and measurement of apo(a) by turbidimetric or nephelometric analysis.

In preferred double antibody assay methods, the amount of immunoreaction product determined is related to the amount of immunoreaction product similarly formed and determined using a standard sample in place of the vascular fluid sample, wherein the standard sample contains a known amount of lipoprotein(a) or apolipoprotein(a) in accordance with this invention. Alternatively, a synthetic secondary standard can be used.

It is also preferred that the second antibody be directed to a site on the lipoprotein(a) or apolipoprotein(a) which is not the same as the site to which the first antibody is directed. For example, the first antibody can be an anti-B-100 antibody, an anti-plasminogen antibody, or another anti-apolipoprotein(a) antibody directed to a site other than that which reacts with the monoclonal antibodies of the present invention.

The vascular fluid sample can be provided as a known or unknown quantity of blood, or a blood derived product such as serum or plasma. The amount of antibody used can be known or unknown. The admixture is maintained under biological assay conditions for a predetermined period of from about a few seconds to about 20 hours at a temperature of from about 4° C. to about 45° C., advantageously room temperature, i.e., about 25° C.

Biological assay conditions are those that maintain the biological activity of the immunochemical reagents of this invention and the lipoprotein(a) and apolipoprotein(a). Those conditions can generally include a temperature range of from about 4° to about 45° C., a pH value range of from about 5 to about 9, and an ionic strength varying from about that of distilled water to about one molar sodium chloride. Upon routine experimentation, other biological assay conditions may be learned. Methods for optimizing such conditions are well known to those skilled in the art.

Another assay format that is preferred is the precipitation assay. In this embodiment, the process comprises formation of an immunoreaction admixture by admixing a vascular fluid sample with a monoclonal antibody of the invention to yield a precipitous immunoreaction product. The antibody can be operatively linked to a solid particulate such as a microparticle or bead, such that when antibody-antigen crosslinking occurs, the particulate matter aggregates, indicating the presence of the target material.

A particularly preferable method is the immunoturbidimetry because of its adaptability to automatic analysis, enabling a large number of samples to be measured at one time. Specifically, an amount of lipoprotein(a) in a sample such as human plasma, human serum, or the like can be determined by adding one or more of the monoclonal antibodies of the present invention to the sample for the reaction and by measuring changes in the absorbance before and after the reaction.

Many other types of assays within the scope of this invention will be readily apparent to those skilled in the art.

A diagnostic system, in kit form, of the present invention generally comprises, in an amount sufficient for at least one assay, a monoclonal antibody of the invention and a means for detecting an immunoreaction product comprising the antibody and apolipoprotein(a), as packaged immunochemical reagents. Instructions for use of a packaged immunochemical reagent are also typically included.

As used herein, the term "packaged" can refer to the use of a solid matrix or material such as glass, plastic, paper, fiber, foil and the like capable of holding within fixed limits an antibody of this invention. Thus, for example, a package can be a glass vial used to contain milligram quantities of a contemplated antibody or it can be a microtiter plate well to which microgram quantities of a contemplated antibody has been operatively affixed. Alternatively, a package could include antibody-coated microparticles entrapped within a porous membrane or embedded in a test strip or dipstick, etc. Alternatively, the antibody can be directly coated onto a membrane, test strip or dipstick, etc. which contacts the sample fluid. Many other possibilities exist and will be readily recognized by those skilled in this art.

Instructions for use typically include a tangible expression describing the reagent concentration or at least one assay method parameter such as the relative amounts of reagent and sample to be admixed, maintenance time periods for reagent/sample admixtures, temperature, buffer conditions and the like.

In preferred embodiments, a diagnostic system of the present invention further includes a label or indicating means capable of signaling the formation of a complex containing an antibody of the present invention.

The word "complex" as used herein refers to the product of a specific binding reaction such as an antibody-antigen or receptor-ligand reaction. Exemplary complexes are immunoreaction products.

As used herein, the terms "label" and "indicating means" in their various grammatical forms refer to single atoms and molecules that are either directly or indirectly involved in the production of a detectable signal to indicate the presence of a complex. Any label or indicating means can be linked to or incorporated in an expressed protein, peptide, or antibody molecule that is part of the present invention, or used separately, and those atoms or molecules can be used alone or in conjunction with additional reagents. Such labels are themselves well known in clinical diagnostic chemistry.

The labeling means can be a fluorescent labeling agent that chemically binds to antibodies or antigens without denaturing them to form a fluorochrome (dye) that is a useful immunofluorescent tracer. Suitable fluorescent labeling agents are fluorochromes such as fluorescein isocyanate (FIC), fluorescein isothiocyante (FITC), 5-dimethylamine-1-natpthalenesulfonyl chloride (DANSC), tetramethylrhodamine isothiocyanate (TRITC), lissamine, rhodamine 8200 sulphonyl chloride (RB 200 SC) and the like. A description of immunofluorescence analysis techniques is found in DeLuca, "Immunofluorescence Analysis," *Antibody As a Tool*, Marchalonis et al., Eds., John Wiley & Sons, Ltd., pp 189–231 (1982), which is incorporated herein by reference.

In preferred embodiments, the indicating group is an enzyme, such as horseradish peroxidase (HRP), glucose oxidase, or the like. In such cases where the principle indicating group is an enzyme such as HRP or glucose oxidase, additional reagents are required to indicate that a receptor-ligand complex (immunoreacant) has formed. Such additional reagents for HRP include hydrogen peroxide and an oxidation dye precursor such as diaminobenzidine. An additional reagent useful with glucose oxidase is 2,2,-azino-di-(3-ethyl-benzthiazoline-G-sulfonic acid) (ABTS).

Radioactive elements are also useful labeling agents and are used illustratively herein. An exemplary radiolabeling agent is a radioactive element that produces gamma ray emissions. Elements which themselves emit gamma rays, such as $^{124}I$, $^{125}I$, $^{128}I$, $^{132}I$ and $^{51}Cr$ represent one class of gamma ray emission-producing radioactive element indicating groups. Particularly preferred is $^{125}I$. Another group of useful labeling means are those elements such as $^{11}C$, $^{18}F$, $^{15}O$ and $^{13}N$ which themselves emit positrons. Also useful is a beta emitter, such as $^{111}$indium or $^{3}H$. Catalytic antibodies which do or do not bind to the activation site region of apolipoprotein(a) can also be employed for labeling purposes.

The linking of labels, i.e., labeling of peptides and proteins is well known in the art. For instance, monoclonal antibodies produced by a hybridoma can be labeled by metabolic incorporation of radioisotope-containing amino acids provided as a component in the culture medium. See, for example, Galfre et al., *Meth. Enzymol.*, 73:3–46 (1981). The techniques of protein conjugation or coupling through activated functional groups are particularly applicable. See, for example, Aurameas et al., *Scand. J. Immunol.*, 8(7):7–23 (1978), Rodwell et al., *Biotech.*, 3:889–894 (1984), and U.S. Pat. No. 4,493,795.

The diagnostic systems can also include, preferably as a separate package, a "specific binding agent," which is a molecular entity capable of selectively binding an antibody or peptide of this invention or a complex containing such a species, but is not itself a peptide or antibody of this invention. Exemplary specific binding agents are second antibody molecules, complement proteins or fragments thereof, S. aureus protein A, and the like. Preferably the specific binding agent binds the antibody or peptide when it is present as part of a complex.

In preferred embodiments, the specific binding agent is labeled. However, when the diagnostic system includes a specific binding agent that is not labeled, the agent is typically used as an amplifying means or reagent. In these embodiments, the labeled specific binding agent is capable of specifically binding the amplifying means when the amplifying means is bound to a complex.

The diagnostic kits of the present invention can be used in an "ELISA" format to detect the quantity of lipoprotein(a) or apolipoprotein(a) in a vascular fluid sample such as blood, serum, or plasma. "ELISA" refers to an enzyme linked immunosorbent assay such as those discussed above, which employ an antibody or antigen bound to a solid phase and an enzyme-antigen or enzyme-antibody conjugate to detect and quantify the amount of an antigen present in a sample. A description of the ELISA technique is found in Chapter 22 of the 4th Edition of *Basic and Clinical Immunology*, D. P. Sites et al., Lange Medical Publications of Los Altos, Calif. (1982), and in U.S. Pat. Nos. 3,654,090, 3,850,752 and 4,016,043, which are all incorporated herein by reference.

Thus, in preferred embodiments, a monoclonal antibody of this invention can be affixed to a solid matrix to form a solid support. A reagent is typically affixed to a solid matrix by adsorption from an aqueous medium although other modes of affixation applicable to proteins and peptides well known to those skilled in the art, can be used.

Useful solid matrices are also well known in the art. Such materials are water insoluble and include the crosslinked dextran available under the trademark SEPHADEX from Pharmacia Fine Chemicals (Piscataway, N.J.); agarose; polystyrene beads about 1 micron to about 5 millimeters in diameter polyvinyl chloride, polystyrene, crosslinked polyacrylamide, nitrocellulose- or nylon-based webs such as sheets, strips or paddles; or tubes, plates or the wells of a microtiter plate such as those made from polystyrene or polyvinylchloride.

The immunoreagents of any diagnostic system described herein can be provided in solution, as a liquid dispersion or as a substantially dry powder, e.g., in lyophilized form. Where the indicating means is an enzyme, the enzyme's substrate can also be provided in a separate package. A solid support such as the above-described microtiter plate and one or more buffers can also be included as separately packaged elements in the diagnostic assay systems of this invention.

The packaging materials discussed herein in relation to diagnostic systems are those customarily utilized in diagnostic systems. Such materials include glass and plastic (e.g., polyethylene, polypropylene and polycarbonate) bottles, vials, plastic and plastic-foil laminated envelopes and the like.

EXAMPLE 1

Isolation and Purification of Lp(a) Particles

For isolation of Lp(a) for immunization, preparation of primary standard and characterization of monoclonal antibodies, blood samples from fasting donors with single band apo(a) phenotypes were collected into 500 ml units containing EDTA at the concentration of 1 mg/ml. Subsequent to the separation of plasma, a preservative mixture containing sodium azide, ε-aminocaproic acid, phenylmethylsulfonyl fluoride, and aprotinin was added at a final concentration of 0.2 mg/ml, 26.5 mg/ml, 0.174 mg/L, 10,000 KIU/L, respectively. An Lp(a) enriched fraction was obtained from plasma collected as described above, by sequential density ultracentrifugation at d 1.050–1.125 g/ml. The resulting fraction was further purified by passage over a 2.5×100 cm sephacryl S-400 column equilibrated with 0.1M Tris pH 8.2, 0.15M NaCl, 1.0 mM EDTA, 0.2M proline, at a flow rate of 18 ml/hr. The elution of protein was monitored at 280 nm. Under these conditions, Lp(a) eluted first, followed by LDL and then HDL. Fractions containing only Lp(a), as determined by agarose gel electrophoresis, were pooled and concentrated using stirred ultrafiltration (Amicon, Beverly, Mass.) and a buffer containing 0.02M Tris, 0.15 m NaCl, 1 mM EDTA, 0.2 mg/ml NaN3, 10,000 KIU/L aprotinin. After an overnight dialysis at 4° C. against the same buffer, purified Lp(a) was stored at 4° C. for no longer than one month. Total protein concentration was determined by a standardized SDS-Lowry procedure as previously reported (Albers et al., 1989).

EXAMPLE 2

Preparation of Anti-apo(a) Monoclonal Antibodies Conforming to This Invention Male Balb/c mice were immunized with purified Lp(a), with each mouse receiving intraperitoneal injections of 100 μg of Lp(a) in Freunds complete adjuvant. The same dose was repeated two weeks later in Freunds incomplete adjuvant. The mouse with the highest antibody titre to Lp(a) as determined by enzyme-linked immunoassay was boosted with intravenous injections of 50 μg of Lp(a) without any adjuvant for three consecutive days before the fusion. After one day interval, splenocytes of the immunized mice are fused with mouse hybridoma cell line SP2/0-Ag 14 in presence of 1 ml PEG-4000. As cell proliferation approached confluency, supernatants were screened at 1:10, 1:100, 1:1000 for the presence of specific antibodies by an enzyme-linked immunoassay in which the wells of the microtiter plates were coated with 300 ng of Lp(a) or LDL. The cells from the positive wells with the highest titre were cloned by limiting dilutions in 96-well microculture plates, yielding 36 stable clones which reacted with Lp(a) but with no reactivity with LDL or plasminogen. Based on their titre to Lp(a) 18 stable clones were selected to be immunochemically characterized. The selected cells are subcloned until indication of monoclonality is achieved. The immunoglobulin class, subclass, and light chain were determined by immunoblotting (Mouse monoclonal antibodies isotyping kit, Amersham, Arlington Heights, Ill.). The epitope specificity of the antibodies was determined by electrophoresis followed by immunoblotting. The monoclonal antibodies were tested against the following antigens: Lp(a), LDL, plasminogen, and a series of recombinant apo(a) species. A clone recognizing Lp(a) and apo(a) but not recognizing plasminogen or Kringle 4 type 2 of apo(a) was selected from the hybridomas. To obtain large amounts of the antibodies, the hybridoma cells were injected into the peritoneal cavity of "pristane primed" Balb/c mice. The ascitic fluids were collected 7–14 days later, centrifuged, and filtered though 0.45 μm filters. The monoclonal antibodies, purified by absorption to Protein A-Sepharose (Affi-Gel Protein A, Bio Rad, Richmond, Calif.) were stored at −70° C. in 2 mg/ml aliquots.

EXAMPLE 3

ELISA Procedure

Polystyrene microtiter plates (Nunc-Immuno Plate Mad Sorp, Inter Mountain Scientific, Bountiful, Utah) are coated with 100 μl of rabbit anti-human Lp(a) antibody (International Enzymes, Fallbrook, Calif.). The coating antibody is diluted to 5 μg/ml in 100 mM $Na_2 CO_2$, pH 9.6 (coating buffer). The plates are gently shaken for one hour at room temperature and then incubated overnight at 4° C. The unbound antibodies are removed by washing the plates three times using the ELISA plate washer (Dynatech, Chantlily, Va.) with phosphate buffered saline (PBS) and blotted. The remaining binding sites in the wells are blocked by the addition of 300 gl of 3% BSA/PBS, and gently shaken at room temperature for one hour, washed as before and blotted. After blocking and washing, the plates are dried by blotting, sealed and stored at 4° C. until use.

After equilibrating plates to room temperature (30 min) 100 μl of each dilution of the standard and samples diluted in PBS containing 0.1% BSA, 0.05% Tween 20, are added to the wells. The calibrator serum ranges from 0.04 μg/ml to 0.7 μg/ml Lp(a) protein; the plasma samples are usually diluted 1:400. For samples with Lp(a) protein values <16 μg/ml samples are diluted 1:20. For samples with Lp(a) protein values >280 μg/ml samples are diluted 1:800 or greater. The microtiter plates are incubated for one hour at room temperature on the shaker, washed three times, and blotted. The plates are then incubated with 100 μl per well of anti-apo(a) monotional antibody a-40 for one hour at room temperature on shaker, washed three times and blotted. To detect the amount of monoclonal antibody bound 100 μl of goat anti-mouse IgG horseradish peroxidase conjugate, 1:2000 dilution (Boehringer Mannheim, Indianapolis, Ind.) is added and the plates incubated for one hour at room temperature. After washing three times in PBS, 100 μl of the substrate (o-phenylenediamine dihydrochloride and hydrogen peroxide in 0.1M citrate) is added to each well. The enzyme reaction is allowed to proceed for 15 minutes at room temperature then the reaction is stopped by adding 2N $H_2SO_4$ to each well, and the absorbance read at 495 nM using a microplate reader (Molecular Devices, Menlo Park, Calif.). The absorbance is plotted against Lp(a)-protein concentration to generate a standard curve from which the concentration of Lp(a) contained in plasma or serum can be determined. An example of a standard curve is shown in FIG. 1. To verify the specificity of the assay purified LDL or plasminogen, at a concentration up to 12.8 μg/ml were found not to be reactive in the assay.

EXAMPLE 4

Comparison of Assay Procedures

Figure 2:
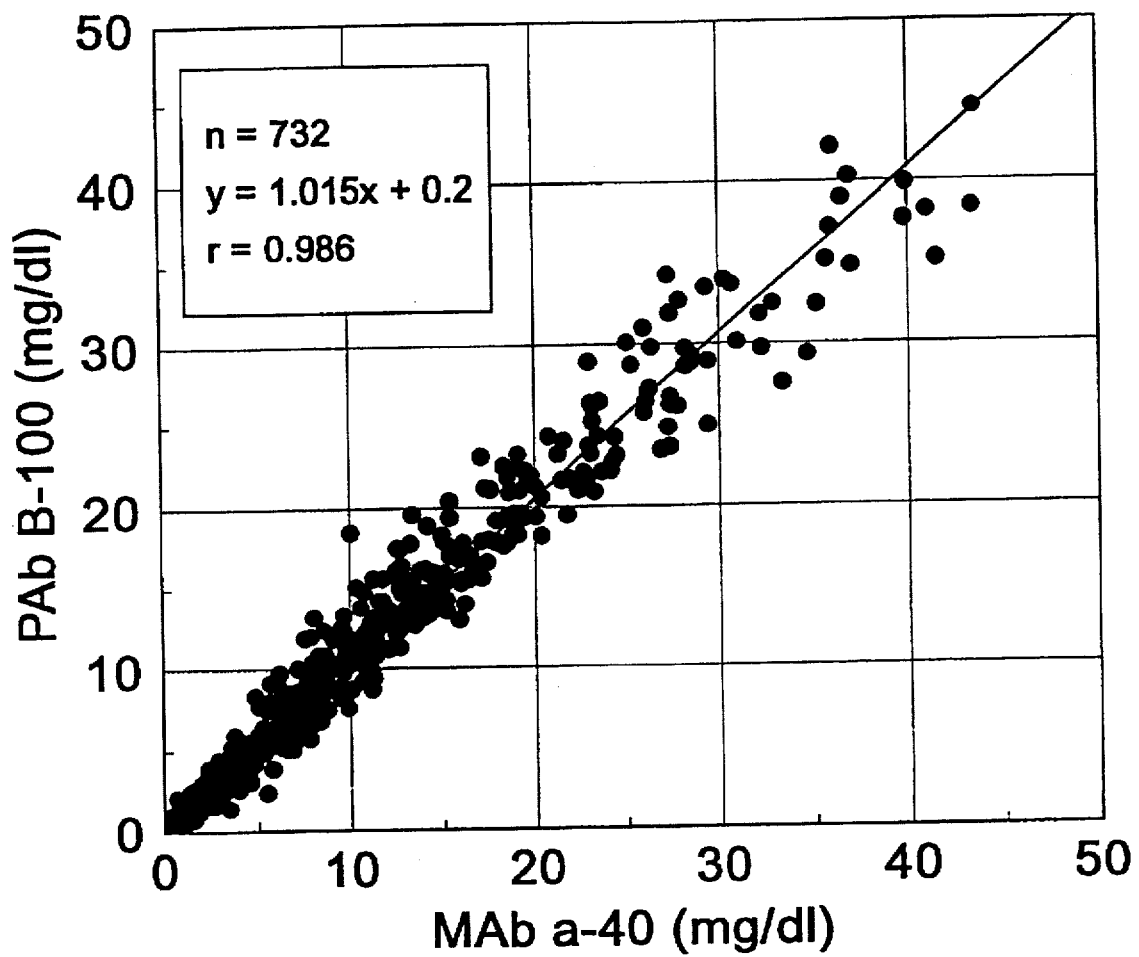
FIG. 2 is a plot of lipoprotein concentrations in test samples (in mg/dl) when measured in assay formats using monoclonal antibody a-40 or sheep polyclonal antibody specific for human apo B as the detecting antibody, in accordance with Example 4.

An experiment was performed to compare Lp(a) measurements according to the present invention with another Lp(a) ELISA sandwich assay that uses anti-apo B as the detecting antibody. This comparative assay was similar to that described in Example 3 except that instead of using anti-apo(a) monoclonal antibody a-40 as the detecting antibody the microtiter plates were incubated with 100 μl per well of polyclonal sheep anti-human apo B conjugated with horseradish peroxidase conjugate (Biodesign, Kenneburkport, Me., 1:3200 dilution) and the amount of antibody bound measured by the addition of the substrate o-phenylenediamine dihydrochloride and reading the absorbance as explained in Example 3. Lp(a) protein levels were measured on 723 plasma samples from subjects who demonstrated a single apo(a) band on a high resolution agarose apo(a) phenotyping system (Marcovina et al., 1993). This group of subjects were selected because they exhibited a wide range of apo(a) size isoforms and Lp(a) concentrations. Nearly identical concentrations of Lp(a) were found when using either antibody MAb a-40 or polyclonal antibody directed to apo B as the detecting antibody (FIG. 2). Linear regression analysis indicated that the two methods were very highly correlated (r=0.986, y=1.015x+0.2). These results indicate that Lp(a) concentrations measured using apo B detection were comparable with those determined by MAb a-40 over a wide range of apo(a) concentrations and apo(a) size.

The foregoing illustrative examples relate to the measurement of apo(a) and lipoprotein(a) in a fluid sample. While the present invention has been described in terms of specific conditions and format it is understood that variations and modifications will occur to those skilled in the art upon consideration of the present invention. For example, while the ELISA procedure of Example 3 involves binding of the first anti-apo(a) antibody to a solid substrate and forming the desired antibody-antigen complex by incubation with a fluid sample followed by washing, it is contemplated that the antibody-antigen complex may be found in solution and subsequently bound to a substrate. Similarly, it is envisioned that various materials for immobilizing anti-apo(a) antibody other than plastic microliter plates (such as polystyrene latex particles, nitrocellulose and other plastic or glass supports such as beads, discs, or tubes will be effective in practice of the present invention.

Furthermore, it will be appreciated by those skilled in the art that a specific assay for apo(a) and Lp(a) can readily be adapted by coupling the specific anti-apo(a) monoclonal antibody a-40 to numerous supports such as latex beads and apo(a) and Lp(a) quantitated by turbidimetric or nephelometric analysis.

Numerous modifications and variations in the invention as described in the above illustrative examples are expected to occur to those skilled in the art.

While the preferred embodiment of the invention has been illustrated and described, it will be appreciated that various changes can be made therein without departing from the spirit and scope of the invention.

REFERENCES

1. Albers, J. J. et al., "The unique lipoprotein(a): Properties and immunochemical measurement," Clin. Chem. 36:2019–2026 (1990).
2. McLean, J. W. et al., "cDNA sequence of human apolipoprotein(a) is homologous to plasminogen," Nature 330:123–137 (1987).
3. Guevara, J. Jr., et al., "A structural assessment of the apo(a) protein of human lipoprotein(a)," Proteins: Struc. Func. Genet. 12:188–199 (1992).
4. van der Hoek, Y. Y. et al., "The apolipoprotein(a) kringle IV repeats which differ from the major repeat kringle are present in variably-sized isoforms," Hum. Mol. Genet. 2:361–366 (1993).
5. Lackner, C. et al., "Molecular definition of the extreme size polymorphism in apolipoprotein(a)," Hum. Mol. Genet. 2:933–994 (1993).
6. Albers, J. J. and Hazzard, W. R., "Immunochemical quantification of human plasma Lp(a) lipoprotein," Lipids 9:15–26 (1974).
7. Albers, J. J. et al., "Radioimmunoassay of human plasma Lp(a) lipoprotein," J. Lipid Res. 18:331–338 (1977).
8. Gaubatz, J. W. et al., "Human plasma lipoprotein(a). Structural properties," J. Biol. Chem. 258:4582–4589 (1983).
9. Rainwater, D. L. and Manis, G. S., "Immunochemical characterization and quantitation of lipoprotein(a) in baboons: Development of an assay depending on two antigenically distinct proteins," Atherosclerosis 73:23–31 (1988).
10. Wong, W. L. T. et al., "A monoclonal-antibody-based enzyme-linked immunosorbent assay of lipoprotein(a)," Clin. Chem. 36:192–197 (1990).
11. VuDac, N. et al., "Latex immunoassay of human serum Lp(a) lipoprotein," J. Lipid Res. 26:267–269 (1985).
12. Cazzolato, G. et al., "The determination of lipoprotein Lp(a) by rate and endpoint nephelometry," Clin. Chim. Acta. 135:203–208 (1983).
13. VuDac, N. et al., "A selective bi-site immunoenzymatic procedure for human Lp(a) lipoprotein quantification using monoclonal antibodies against apo(a) and apo B," J. Lipid Res. 30:1437–1443 (1989).
14. Albers, J. J. et al., "Evaluation of a monoclonal antibody-based enzyme-linked immunosorbent assay as a candidate reference method for the measurement of apolipoprotein B-100," J. Lipid Res. 30:1445–1458 (1989).
15. Marcovina, S. M. et al., "Identification of 34 apolipoprotein(a) isoforms: Differential expression of apolipoprotein(a) alleles between American Blacks and Whites," Biochem. Biophys. Res. Commun. 191:1192–1196 (1993).

The embodiments of the invention in which an exclusive property or privilege is claimed are defined as follows:

1. A monoclonal antibody produced by the hybridoma ATCC No. CRL 11759.
2. The hybridoma ATCC No. CRL 11759.

* * * * *